(12) United States Patent
Missotten et al.

(10) Patent No.: US 7,584,663 B2
(45) Date of Patent: Sep. 8, 2009

(54) MATERIAL STREAM SENSORS

(75) Inventors: Bart M. A. Missotten, Herent (BE); Pieter W. J. Calmeyn, Sint-Joris-Weert (BE); Bart De Ketelaere, Boechout (BE)

(73) Assignee: CNH America LLC, New Holland, PA (US)

( * ) Notice: Subject to any disclaimer, the term of this patent is extended or adjusted under 35 U.S.C. 154(b) by 277 days.

(21) Appl. No.: 11/713,918

(22) Filed: Mar. 5, 2007

(65) Prior Publication Data
US 2007/0209423 A1    Sep. 13, 2007

(30) Foreign Application Priority Data
Mar. 10, 2006  (GB) .................................. 0604860.7

(51) Int. Cl.
*G01N 29/12* (2006.01)
*A01D 75/02* (2006.01)

(52) U.S. Cl. .................. 73/579; 73/12.11; 209/599; 460/2; 460/45

(58) Field of Classification Search ............ 73/579, 73/587
See application file for complete search history.

(56) References Cited

U.S. PATENT DOCUMENTS

| | | | | |
|---|---|---|---|---|
| 4,000,398 A | * | 12/1976 | Conner | 377/6 |
| 4,004,289 A | * | 1/1977 | Kirk | 73/861.21 |
| 4,275,546 A | * | 6/1981 | Bohman et al. | 460/2 |
| 4,466,543 A | * | 8/1984 | Zwahlen et al. | 209/556 |
| 4,490,964 A | * | 1/1985 | Eldredge | 460/5 |
| 4,625,872 A | * | 12/1986 | DeLacy et al. | 209/557 |
| 4,651,331 A | * | 3/1987 | Harrsen et al. | 377/6 |
| 5,046,362 A | * | 9/1991 | Strubbe | 73/579 |
| 2005/0137003 A1 | * | 6/2005 | Behnke et al. | 460/1 |

FOREIGN PATENT DOCUMENTS

EP    0339140 B1 *  9/1993
EP    0347979 B1 * 10/1993

* cited by examiner

*Primary Examiner*—Hezron Williams
*Assistant Examiner*—Rose M Miller
(74) *Attorney, Agent, or Firm*—Michael G. Harms; John William Stader; Patrick M. Sheldrake

(57) ABSTRACT

A method of determining the content of a desired component in a stream of material including two or more types of component, includes causing or permitting a stream of a plurality of particles of material to impact a sensor member located in a path of the material thereby inducing vibration of the sensor member, analyzing vibrations of the sensor member and from the analysis determining whether individual impacts caused by the stream are one of any two or more types selected from three possible impact types, and performing an operation based on the result of the analysis.

19 Claims, 7 Drawing Sheets

MATERIAL STREAM SENSORS

CROSS REFERENCE TO RELATED APPLICATIONS

This Patent Application claims priority under 35 U.S.C. § 119 to GB 0604860.7, filed on Mar. 10, 2004 titled, "Improvements in or relating to Material Stream Sensors" and having Bart M. A. Missotten, Pieter W. J. Calmeyn and Bart De Ketelaere as inventors. The full disclosure of GB 0604860.7 is hereby fully incorporated herein by reference.

This invention concerns material stream sensors and particularly (but not exclusively) grain sensors that are used in grain (or other crop) flow or handling paths.

Material stream sensors in the form of grain loss sensors are used at various locations in harvesting machines, especially combine harvesters. In such machines during use some loss of grain kernels, being the desired part of a harvested crop, occurs. The loss occurs by grains falling from the harvesting machine to the ground (or to inaccessible parts of the interior of the machine), from where they cannot economically be collected.

The loss of even a small amount of grain is undesirable, for various reasons including the reduction in revenue, to the farmer, that grain loss represents.

Many modern designs of combine harvesters include a grain loss sensor whose function is to estimate the amount of grain lost during harvesting operations. Typically the grain loss sensor comprises a flat metal plate (a "sensor plate") located beneath a part of a grain handling path where grain loss is known to occur during harvesting operations. The sensor plate includes mounted thereon or embedded below its surface one or more piezoelectric crystals. As grain falls onto the plate the distortion of the latter induces voltages in the piezoelectric crystals. The voltages are approximately proportional to the amounts of grain being lost per unit time. The voltages may be transmitted externally of the plate as signals indicative of the degree of grain loss at a given time.

Such known grain loss sensors are unacceptably inaccurate.

An inaccurate grain loss signal could cause a harvester operator to make inappropriate adjustments to sub-systems of the machine, during harvesting, in a misguided attempt to correct a perceived level of grain loss.

Typically the grain loss sensor is located towards the rear of a section of a combine harvester, such that it detects grain lost "downstream" of e.g. the cleaning section. As a result, any lost grain detected by the sensor may be mingled with other components of a material stream that are rejected by the cleaning section and are ejected rearwardly from the combine harvester.

In the case of wheat harvesting, any grain may at the location of the grain loss sensor be mingled predominantly with straw.

If straw falls in a horizontal (or predominantly horizontal) orientation onto a grain loss sensor it produces in the sensor plate (and hence the piezoelectric crystals) a frequency response that differs from the response induced by the impact of grains. Filtering of the signals produced by the piezoelectric crystals in prior art arrangements therefore may be capable of eliminating the effects of horizontally-falling straw.

However a length of straw that falls vertically (or predominantly vertically) onto the sensor plate produces a different frequency response.

A length of straw tends to break off adjacent a node of the plant, i.e. the thickened stem portion from where a leave arises. Thus many of the pieces of straw in a combine harvester include the node at one end. The node in a mature plant is somewhat rigid. If, as is commonly the case, a piece of straw falls onto the sensor plate of a grain loss sensor "tip first" (i.e. so that the node strikes the plate) the frequency response of the sensor plate is similar to that produced when a grain impacts the plate. The prior art techniques for filtering out impacts caused by horizontally falling straw are not adequate to distinguish between grain impacts and straw tip impacts.

Furthermore the prior art philosophy exclusively concerns estimating the amount of grain loss occurring at a particular time during harvesting operations.

According to the invention there is provided a method of determining the content of a desired component in a stream of material including two or more types of component, comprising the steps of:

causing or permitting a said stream, comprising plural particles of material, to impact a sensor member located in a path of the material thereby inducing vibration of the sensor member;
  analysing vibrations of the sensor member and from the analysis determining whether individual impacts caused by the stream are one of any two or more types selected from three possible impact types; and
  performing an operation based on the result of the analysis.

Preferably the three impact types are grain impacts, straw impacts and straw tip impacts.

The terms "grain impacts", "straw impacts" and "straw tip impacts" are of particular relevance when considering analyses carried out, in accordance with the invention, on the products of a cereal harvesting operation.

Thus a grain impact occurs when a wheat or other cereal kernel impacts a sensor plate; a straw impact relates to the situation of a non-tip part of a straw impacting the sensor plate; and a straw tip impact (as its name implies) concerns impact of a relatively hard or rigid straw tip, including a node, with the sensor plate.

The invention however is applicable to other types of harvesting operation, not involving cereals. In such cases the invention would seek to distinguish between other types of impact than those stated.

The invention further is applicable to non-harvesting operations in which streams of material flow from one place to another, the streams including respective components that induce vibrative responses in a sensor plate when impacting such a plate.

Regardless of the precise type of material stream under consideration, however, the invention in its broadest form as stated above is advantageous in improving the accuracy of material stream sensors when distinguishing between different types of material component some of which produce similar frequency responses in a sensor plate or similar member.

Optionally the method includes the step of analysing vibrations of the sensor member in a frequency range exceeding 25 kHz.

In this regard it has been found that prior art grain loss sensors (in particular) are subject to inaccuracy because they do not assess the frequency response of a sensor plate in frequency ranges exceeding 20 kHz. Analysing, in accordance with the invention, in frequency ranges exceeding 25 kHz, and preferably up to 50 kHz, provides additional data, compared with the prior art sensors, allowing better discrimination between impact types.

Preferably the step of performing an operation includes the steps of generating a grain loss signal indicative of the amount of grain in the stream and a MOG signal that is indicative of the amount of material other than grain (MOG) in the stream, and correcting the grain loss signal in dependence on the MOG signal.

This aspect of the invention relates to an advantage not previously contemplated using prior art arrangements.

The aim of all the prior art grain loss sensors has been to gauge the amount of grain loss at any time during harvesting. A novel control philosophy, involving adjusting or correcting a grain loss signal in dependence on the amount of MOG in the stream of material being sensed, can lead to more accurate machine control than has been possible in the prior art. This is especially so in preferred embodiments of the method of the invention, in which the MOG signal includes one or more components indicative of straw impacts and one or more components indicative of straw tip impacts.

One option within the scope of the invention is to include the step of causing a display device to display information related to the grain loss signal. Such a display may be conveniently located in the cab of the combine harvester, or elsewhere.

Additionally or alternatively the method may include the step of generating one or more control commands in dependence on the grain loss signal and/or the MOG signal. Preferably the or each control command is selected from the list including:

a. a cleaning section sieve opening command;
b. a cleaning section sieve closing command; and/or
c. a fan speed command.

As a consequence of these steps the method of the invention may advantageously employ either the grain loss signal or the MOG content in the material stream (as determined from the sensor output) to indicate whether overloading of the cleaning section of the harvester has occurred or is about to occur.

This ability has not been available at all in the prior art. It represents a significant improvement in the control of harvesting machines.

In this connection it has been found by the inventors that the amount of MOG in the material stream ejected by the cleaning section is a good indicator of impending overloading of the cleaning section. The ability to adjust the cleaning section in dependence on the grain loss sensor output therefore provides the chance to take corrective action before the overloading becomes problematic.

It is particularly helpful therefore that the grain loss signal generated according to the method of the invention is more accurate than those of the prior art methods, since it is then possible more accurately to determine the MOG content of the material stream.

Conveniently the sensor member includes a transducer that is capable of generating electrical signals that are indicative of its vibration; and the method includes deriving from the electrical signals variables that are related to vibrations of the sensor member, the step of analysing vibrations of the sensor member including the step of processing the variables according to an algorithm containing arithmetic terms and parameters, the parameters being related to characteristics of three different types of impact respectively.

It is also preferable that method includes the step of making linear and/or non-linear combinations of the processed variables; and that the parameters of the algorithm are selected and/or combined as a result of one or more of:

a. Genetic algorithm techniques;
b. Linear and/or non-linear regression techniques;
c. Tree-based modelling;
d. Analysis of variance techniques;
e. Canonical discrimination.

Although such techniques for establishing the parameters of an algorithm are in themselves known, in the context of the method as defined hereinabove they are unique.

The use of the listed techniques to establish the parameters that are processed using the algorithm and/or the nature of the algorithm itself is particularly beneficial, firstly since the result is a set of parameters that are known to be strongly related to the quantities being detected or measured using the method of the invention. This means in turn that the algorithm is efficient in the sense that it does not waste processor effort in calculating on the basis of parameters that have little influence over the result to be determined.

Also, selection of the parameters using one or more of the aforementioned techniques results in parameters that are "robust", i.e. that do not induce instability or error into operation of the algorithm.

During use of the algorithm in accordance with the steps of the method it is possible to contemplate analysis based either on time domain division or frequency domain division. The inventors have found that good results are obtainable using either approach.

To this end therefore in one embodiment of the method of the invention the variables relate to the vibration of the sensor member in two consecutive periods following impact of a particle of the stream of material.

More particularly, in a preferred embodiment of the method the variables relate to the variance in the amplitude of vibration of the plate during each of the two consecutive periods, especially the first and second half-milliseconds following impact respectively.

The use of such a short timing period is associated with at least two important advantages of the method of the invention, as follows:

a. the overall sampling period is short (1 millisecond) leading to a very rapid processing rate. Thus the method of the invention is capable of producing outputs much more quickly than the prior art methods; and
b. during the first millisecond of vibration of a sensor plate following the impact of e.g. a grain or another particle in the material stream, the effects of the impact predominate. During subsequent time periods the vibration of the sensor plate at its natural frequency (or at a frequency forced by vibrations of rotary components of the harvesting machine) induces noise that makes it difficult to distinguish the effects of the grain, etc. impacts.

In one preferred form of the method of the invention in the algorithm the variable related to vibration in the second of the consecutive periods is subtracted from the variable related to vibration in the first period, in order to provide an output indicative of the type of impact sustained by the sensor plate at the beginning of the sampling period in question.

In an alternative embodiment of the method in the algorithm the variable related to vibration in the first period is divided by the variable related to vibration in the second period.

The use of frequency domain division as indicated above is an alternative to the use of time domain division. Thus in accordance with another preferred aspect of the invention the chosen variables are respectively related to the energy of vibration of the sensor member in upper and lower, distinct frequency bands. The energy levels are detected during a sampling period that may be, for example, 1 millisecond in preferred embodiments of the method of the invention.

More particularly in a preferred version of the algorithm the variable related to the energy of vibration in the upper frequency band is divided by the variable related to the energy of vibration in the lower frequency band. Such a technique also has been found to produce reliable, accurate results in a short processing period.

Preferably the upper frequency band is approximately 30-40 kHz, and the lower frequency band is approximately 2-10 kHz.

In this regard the inventors have surprisingly discovered that in the 30-40 kHz frequency band there is contained considerable data that are useful for distinguishing between grain impacts, straw impacts and straw tip impacts for example. The prior art grain loss sensors however employ sensing members (e.g. piezoelectric crystals, as indicated) that operate in a frequency range up to approximately 20 kHz.

An analysis method in accordance with the invention that involves arithmetic combinations, of the data relating to the two frequency ranges, which accentuate the differences between the data in the respective ranges is particularly good for distinguishing between impact types.

Overall, use of the method of the invention has been found to be highly successful at distinguishing the different types of impact that may arise in a grain loss sensor or a similar device used for material stream sensing. The height from which the particles fall to impact the sensor plate has been found, as a result of careful selection of the parameters of the algorithm employed as part of the method, to have little influence over the accuracy of the method. This is because the parameters chosen are as far as possible independent of the initial energy of the impact.

Furthermore the selection of the parameters can make the method of the invention largely insensitive to the hardness and rigidity of the particles in the stream of material. This also is important in a harvesting operation since variations in the moisture of crop affect the physical properties of the grains, and especially the hardness.

According to a further aspect of the invention there is provided an apparatus, for determining the content of MOG in a stream of material, comprising a sensor member that is vibrative when impacted and having operatively connected thereto a transducer that is capable of generating one or more signals in dependence on vibration of the sensor member; and a processor that is operatively connected to receive the signals from the transducer and is programmed to perform the method steps defined hereinabove.

The transducer may preferably be selected from the group comprising a piezoelectric transducer, an accelerometer, a microphone, a knock sensor, a laser vibrometer and a high-speed camera. From this group accelerometers are the most preferred at the present time since they are robust and hence can withstand the highly variable environment of the interior of a combine harvester. Moreover several accelerometers have been developed that economically provide good accuracy and short sampling gates.

There now follows a description of preferred embodiments of the invention, by way of non-limiting example, with reference being made to the accompanying drawings in which.

Figure 1:
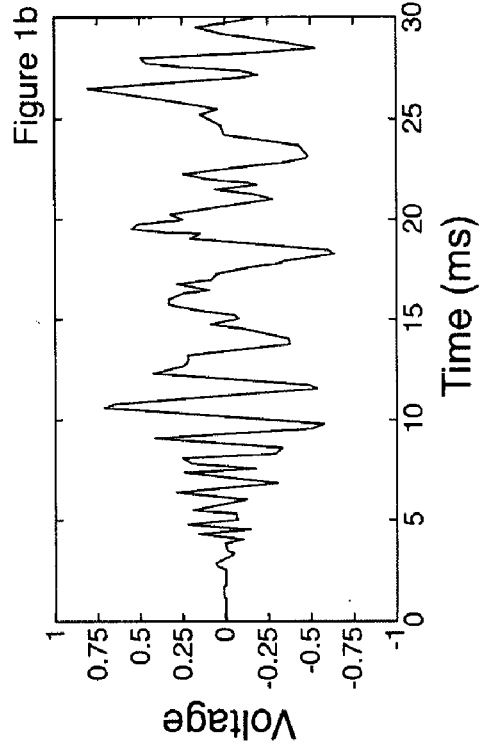
FIGS. 1a-1d is a series of plots of the response of a sensor plate of a grain loss sensor when subject to a grain impact and a straw impact, respectively.
Figure 1:
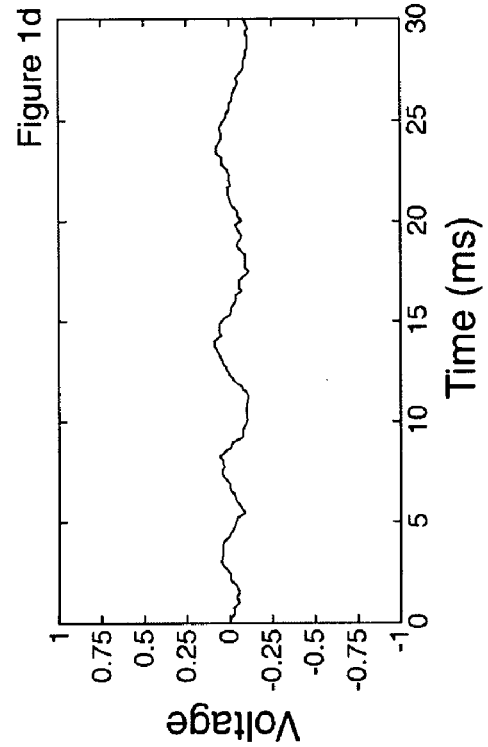
Figure 1:
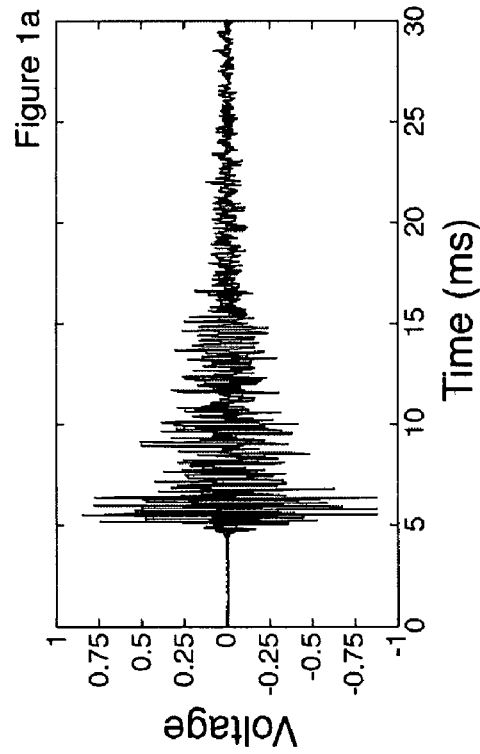
Figure 1:
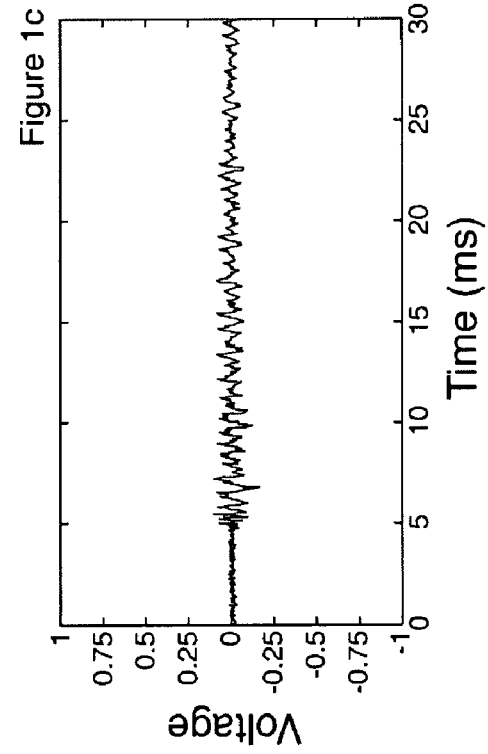

Referring to the drawings, FIG. 1 shows the typical amplitude response of a sensor plate of a grain loss sensor when impacted respectively by a comparatively hard object, such as a grain kernel; and an object such as a length of straw landing horizontally, or predominantly horizontally. FIGS. 1a and 1b show the amplitude response (indicated as a voltage output of a transducer) for the grain impact; and FIGS. 1c and d the amplitude response for the straw impact.

In FIG. 1, FIGS. 1a and 1c represent the pure output of the transducer; and FIGS. 1b and 1d the output following filtering of certain noise components.

As is evident from FIG. 1, the amplitude responses of these two types of impact are comparatively distinct, such that it would be relatively easy to distinguish between the two impact types. This is because the response in the first few milliseconds after impact of the harder particle such as a grain kernel has high values for the peak amplitude voltage, whereas the impact of the straw induces lower peak amplitude values in the plate.

Therefore an analysis based on peak amplitude levels might be adequate to distinguish between the two impact types. This could be one way of operating in accordance with prior art grain loss sensing methods.

However this approach only holds good for impacts that induce responses, in the sensor plate of a grain loss (or other material stream) sensor, that are dramatically different as exemplified by FIG. 1. In cases of the responses being similar such an analysis is less acceptable.

Figure 2:
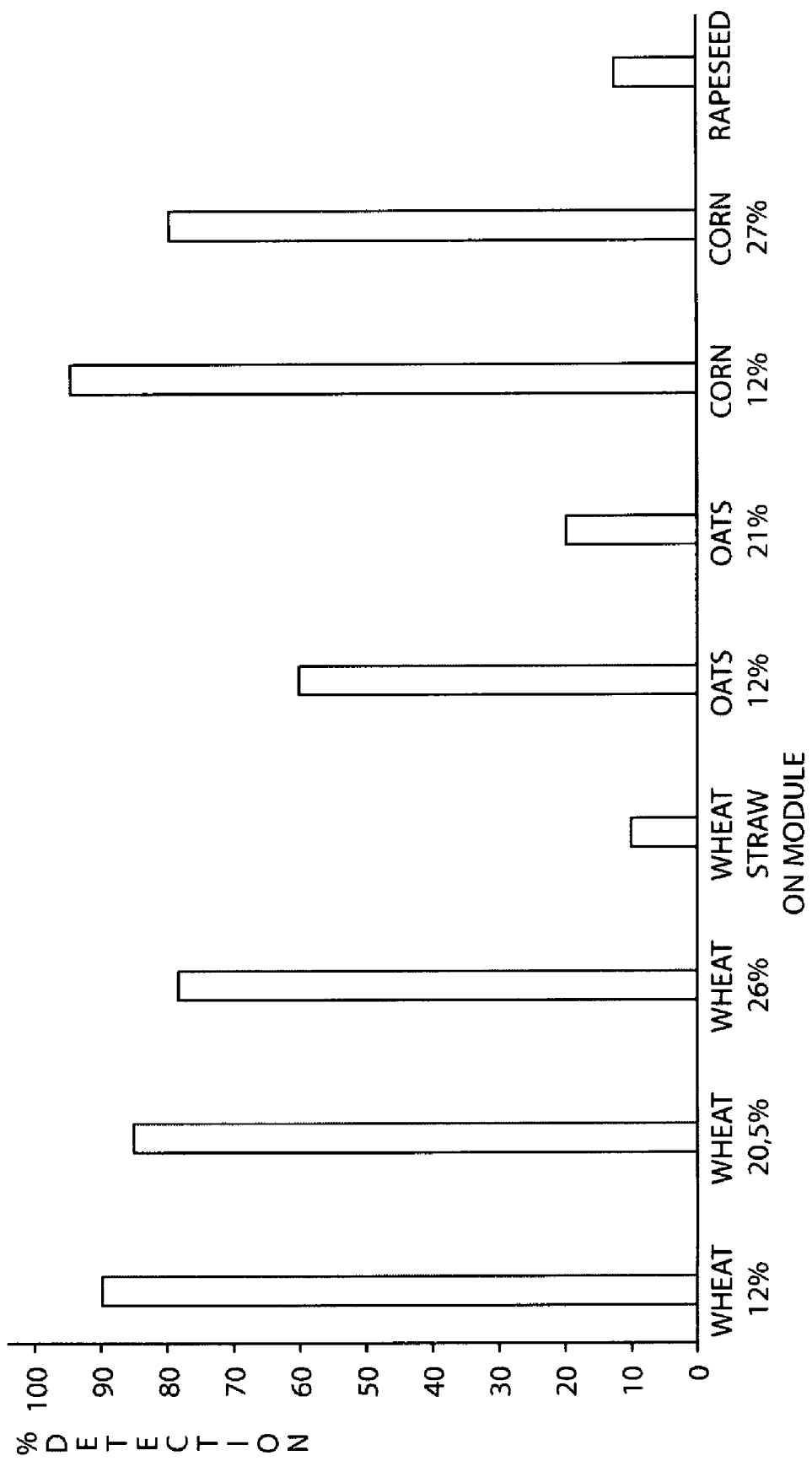
FIG. 2 shows the effectiveness of prior art grain loss sensors in identifying particular types of impact, including straw tip impacts (labelled as "wheat straw on node" impacts in FIG. 2)

This is illustrated graphically in FIG. 2, in which are plotted indications of the ability of a prior art grain loss sensor to identify impacts of various types. As is shown in FIG. 2 for example the success in detecting straw tip impacts ("straw node" impacts) is low.

This is because the amplitude response of the sensor plate is closely similar, in terms of the peak amplitudes, regardless of whether the impact is of a grain kernel or a straw tip. Therefore it is impossible using prior art techniques reliably to identify straw tip impacts. As a result the grain loss signal is misleading. This gives rise to the disadvantages set out above.

Figure 3:
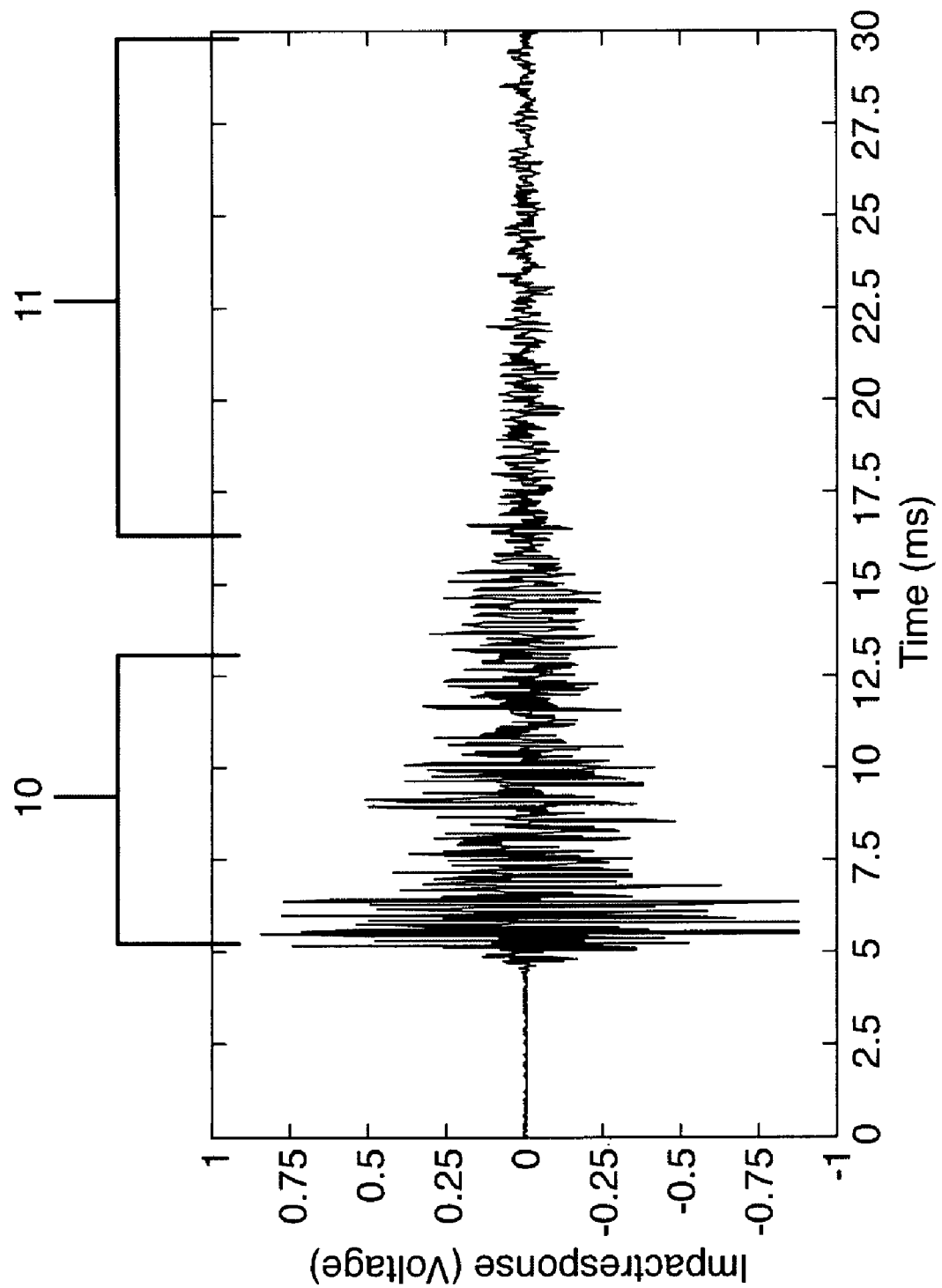
FIG. 3 shows in more detail the amplitude response of the sensor plate for grain impacts or straw tip impacts.

FIG. 3 shows in more the amplitude response of the sensor plate of a grain loss (or other material stream) sensor, in the period following an impact by a particle such as a grain kernel. The inventors have discovered that the initial period of the response is influenced predominantly by the impact; and the subsequent period by characteristics of the sensor plate itself. These two parts of the response are indicated by reference numerals 10 and 11 in FIG. 3.

The response following an impact of a straw tip at a node is similar to that shown in FIG. 3. On the face of it therefore it is difficult to distinguish between grain impacts on the one hand and straw tip impacts on the other, merely by analysing peak amplitude values of the response plot.

The method of the invention however involves discriminating between two impact types selected from a set of three impact types, thereby providing for more accurate sensing of the types of impact. Thus the method of the invention has been found to be particularly successful when a stream of material, comprising plural particles, is permitted to impact onto a sensor plate in the path of the material such that vibration of the sensor member results; and subsequently an analysis takes place on the basis of the foregoing principle of identifying two possible impact types out of a set of three or more such impact types.

This is achieved in the preferred embodiments of the invention either using an analysis technique based on a time-domain division of the output of the transducer; or a frequency-domain division.

Considering firstly the version of the method of the invention based on time-domain division, the inventors have discovered that in the first millisecond (or, in other embodiments, another period) after the impact occurs there are differences in the data presented by grain impacts on the one hand; and straw tip impacts on the other.

These differences are not apparent from simple viewing of FIG. 3, but instead emerge following the adoption of an analysis technique as specified herein.

In particular the time-domain analysis relies on assessing the variance of the transducer output (which is proportional to the vibration of the sensor plate) during the sampling period. The differences between the grain impacts and the straw tip impacts become apparent when considering such variance in the first half of the sampling period and the second half respectively.

Any analytical technique involving the variances during such sub-divisions of the sampling period should be such as to emphasise or enhance the differences between the impact types. In accordance with the invention such enhancement is achieved most effectively either by subtracting the amplitude variance in the second half of the sampling period from the amplitude variance in the first half; or by dividing the variance in the first half of the period by the variance in the second half.

In the preferred embodiment of the method the sampling period is 1 millisecond, whereby the variance periods that are subjected to the arithmetic operations described above are each of half a millisecond in duration.

Either when using the subtractive technique or the divisional technique described above it has been found that the results are highly distinctive of the different types of impact, notwithstanding the apparent similarity of the amplitude responses when plotted against time as in FIG. 3.

Figure 4:
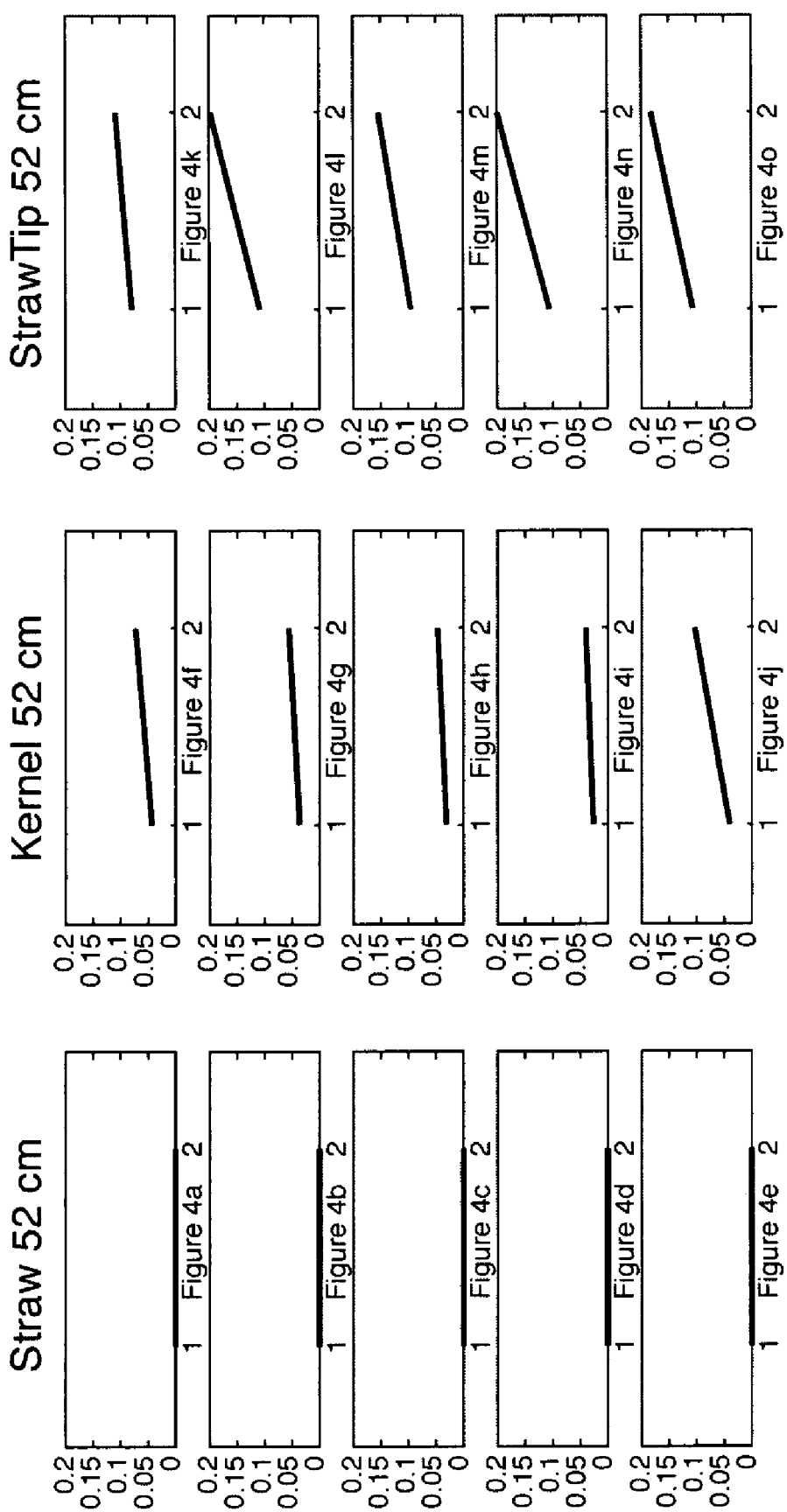
FIG. 4 shows a result of practising the method of the invention in order to distinguish between straw impacts, grain impacts and straw tip impacts, when the basis of the algorithm is a time division analysis.

The starkness of the differences is best illustrated in FIG. 4, which shows that during the first millisecond the evolution of the amplitude for a straw impact is considerably less than that for a grain impact, which in turn surprisingly is less pronounced than that for a straw tip impact.

In more detail, in FIG. 4 the plots 4a-4o are of five impacts of each type and show that the differences between the signal variances in the two sampling periods in each case are least pronounced for straw impacts (FIGS. 4a-4e) and most pronounced for straw tip impacts (FIGS. 4k-4o), with the kernel impacts (FIGS. 4f-4j) showing an intermediate characteristic.

In the plots of FIG. 4 the value at numeral 1 is the signal variance during the first sampling period of half a millisecond. At numeral 2 the signal variance during the consecutive sampling period of half a millisecond is represented. The impact types may already be derived from the variance values themselves or from subtracting the second variance value from the first. An enhanced analysis method involves dividing the signal variance in the second half-millisecond by the signal variance in the first half-millisecond, such that the resulting quotient is of a higher value than the initial variance value. This approach yields dimensionless variables, which is desirable since dimensionless outputs are less sensitive to the initial energy values of the particles, than outputs characterised by dimensions, such as amplitudes.

The differences between the impact types are clear from visual inspection of FIGS. 4a-4o, and can of course be equally easily identified using computational techniques (such as but not limited to subtractions or divisions of the values at 1 and 2 in the plots in FIGS. 4a-4o).

In any event it is clear from FIG. 4 that the method of the invention when embodied as a time-domain analysis is capable of readily distinguishing between the three types of impact used as examples herein.

The frequency domain approach described above also is highly successful, although it is slightly less easy to illustrate using monochrome representations such as FIGS. 5a-5d.

These figures show the energy levels of the sensor plate when plotted in the frequency domain (y-axis) relative to time after impact (x-axis). Probably the most significant part of FIGS. 5a-5d, from the viewpoint of analysis of the stream of material, is the circled part of the upper left quadrant of FIG. 5a (labelled 12 in the Figures). The energy levels actually plotted are mean values resulting from a plurality of tests.

The circled portion 12 is of a lighter shade than the remainder of plot 5a, signifying that the sensor plate has a characteristic energy value in approximately the 25 kHz-50 kHz frequency band, when impacted by a wheat kernel. Thus analysing the energy levels in the 25-50 kHz band reveals information that uniquely identifies grain impacts.

When the grains are moist there is a reduced characteristic portion of the energy levels in the upper left quadrant. This is apparent from FIG. 5b, which plots the results for wheat grains having higher moisture contents than the FIG. 5a grains. However this need not be problematic since the energy level plot for humid wheat in the 20 kHz-50 kHz frequency band while on average lower than for dry grains remains characteristic. Therefore by considering the absolute energy level it is possible to distinguish dry and wet grain impacts.

Figure 5:
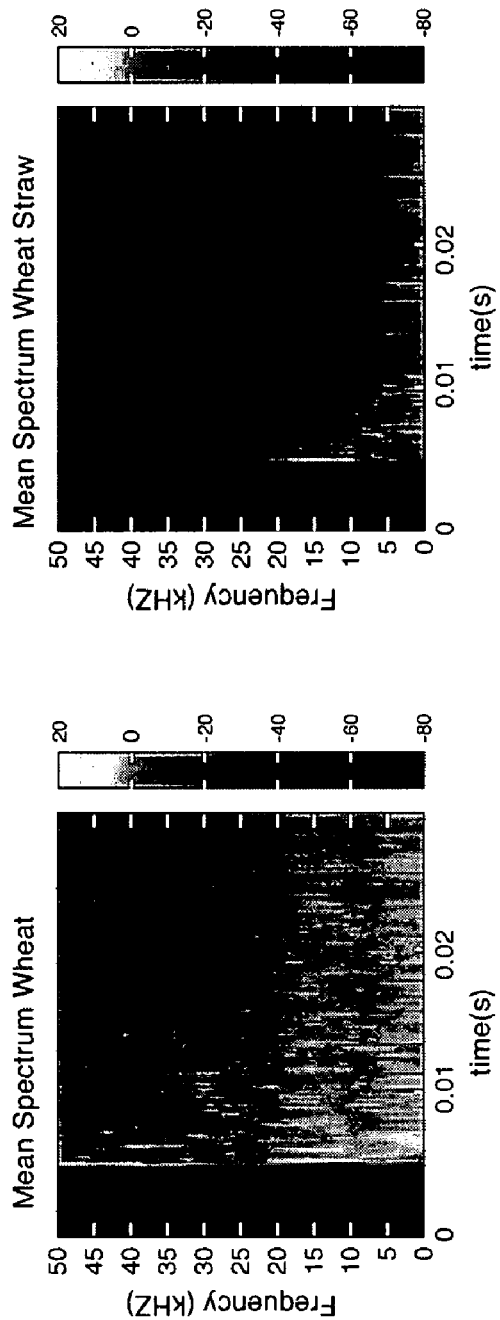
FIG. 5 shows similar results to FIG. 3, when the algorithm used in the method of the invention is based on frequency domain division.
Figure 5:
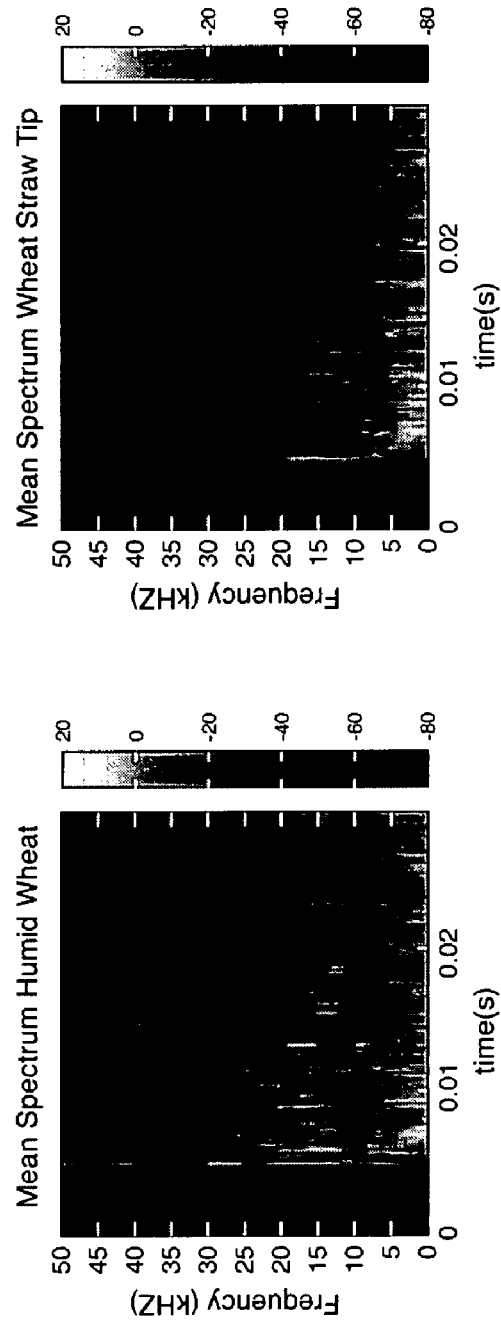

The two grain impact plots 5a and 5b are distinct from FIGS. 5c (straw impacts) and 5d (straw tip impacts) in the 0-20 kHz frequency range, as is evident from comparison between FIGS. 5a, 5b, 5c and 5d.

As described hereinabove, prior art grain loss sensors are capable of detecting the frequency responses only in the range up to 20 kHz. Therefore such sensors would (by reason of omitting data on the 25-50 kHz frequency band forming part of the invention) be incapable of on the one hand distinguishing dry and moist grains from one another; and on the other hand from distinguishing grain impacts from straw and straw tip impacts.

The frequency domain energy level data are in the preferred embodiment of the method of the invention treated using an algorithm such that the energy level values in the higher frequency band (e.g 30-40 kHz, and in any event greater than 25 kHz) are divided by the energy level values in the lower frequency band (e.g. 2-10 kHz and in any event less than 20 kHz). Other arithmetic techniques are possible, the requirement being merely that the manipulation enhances any contrasts between the different parts of the frequency plots, such that the impact characteristics may be easily distinguished.

Figure 6:
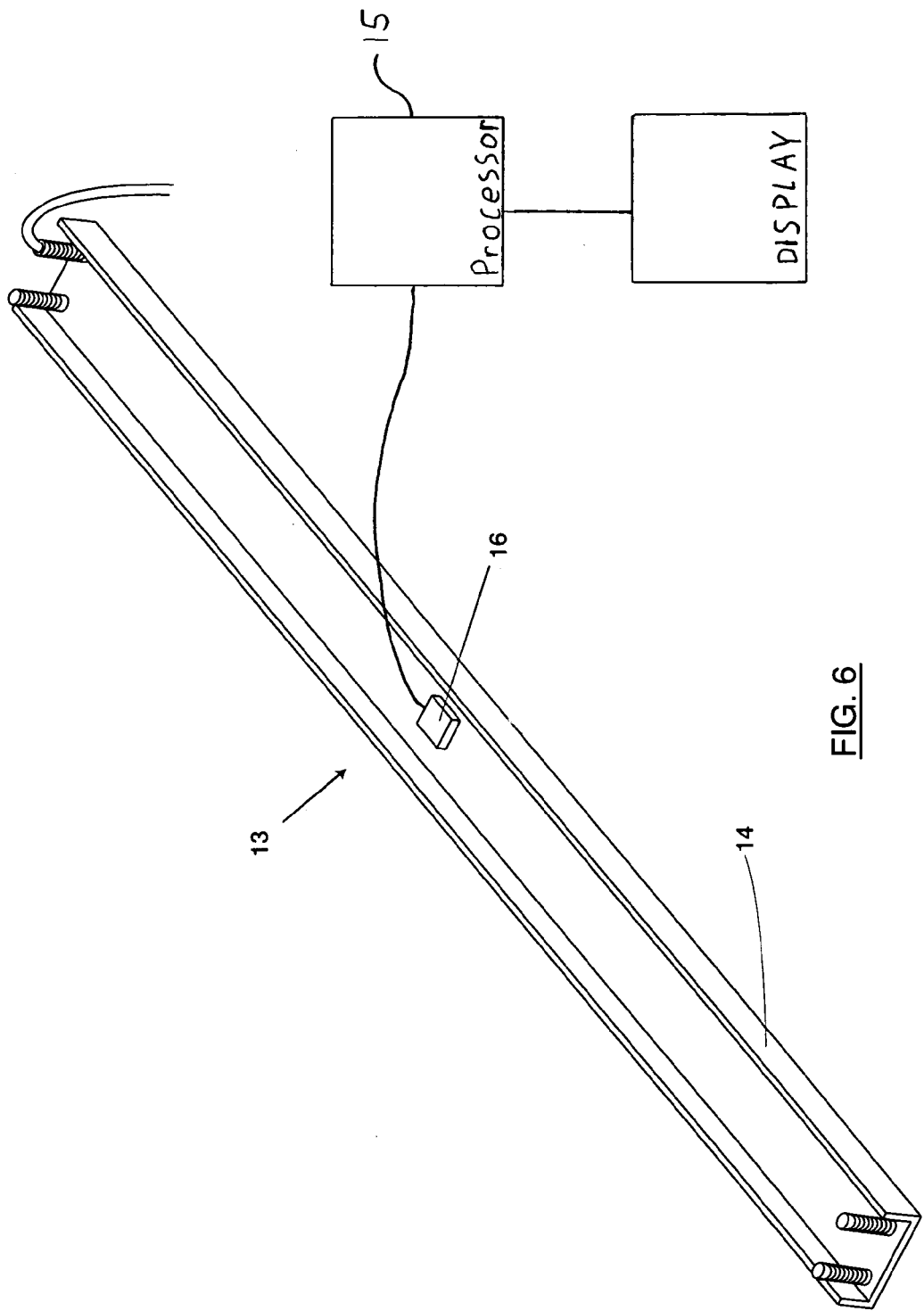
FIG. 6 is a back view of apparatus in accordance with the invention.

Referring now to FIG. 6, a grain loss sensor 13 according to the invention is shown. This includes a generally flat, rectangular metal plate 14 the length of which is approximately the same as the width of a crop material (grain plus MOG) path in a combine harvester.

The plate 14 may be located so as to span such a path whereby lost grain and other material may fall onto it from a height determined by the dimensions of the particular part of the combine harvester under consideration.

Located approximately centrally in the backside of the plate 14 (or at another location thereon in other embodiments) is at least one sensing transducer 16 such as an accelerometer, although as noted herein other types of transducer are theoretically possible within the scope of the invention.

The transducer 16 is connected as needed to an electronics package that is not visible in FIG. 6. A cable connects the output of the transducer, as necessary after conditioning by the electronics package, to a processor 15 for treatment in accordance with the algorithm of the method of the invention.

Figure 7:
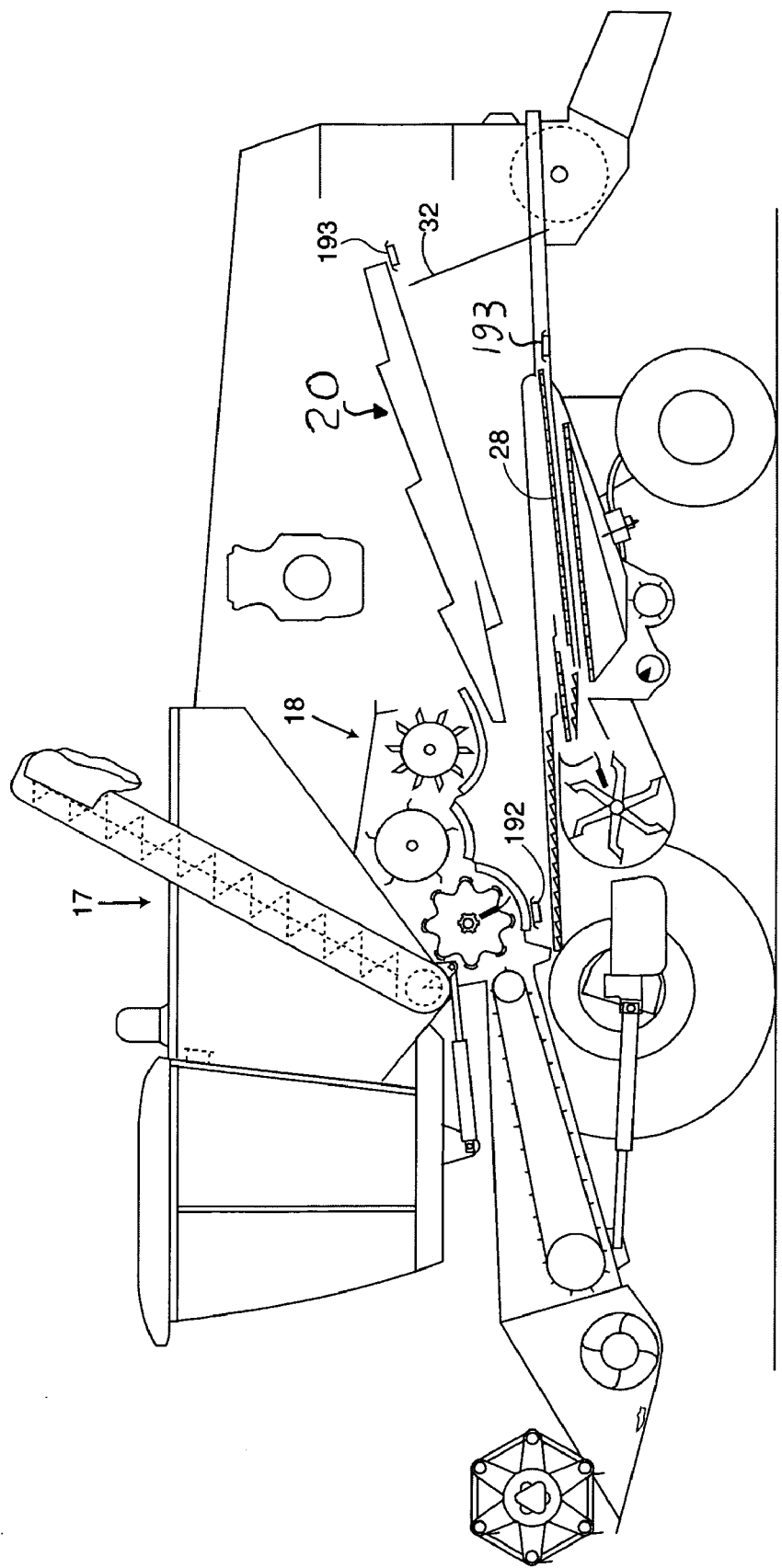
FIG. 7 shows some typical locations of grain sensors in a combine harvester.

The sensor 13 may be located at any of a range of locations in a combine harvester 17 shown in FIG. 7. Thus the sensor 13 may lie for example beneath the threshing section 18 of such a machine, as signified by numeral 192 in FIG. 7; beneath the end of a straw walker 20, as signified by numeral 193; or at the discharge end of an upper sieve 28, as signified by numeral 193. Such sensor may also be installed beneath other crop processing sections, such as the axial separator. It may also be used for assessing the tailings flow at the end of the lower sieve. These are all locations at which an assessment of the amount of grain kernels, and the content of MOG in the material stream, can be useful from the viewpoint of deriving control commands, for the sub-systems of the combine harvester, that enhance the efficiency of the harvesting operation.

Thus during use of the combine harvester 17 a stream of material may fall onto the sensor 13 thereby inducing impact-related vibrations. Analysis of the vibrations in accordance with the techniques of the method of the invention allows the software of the combine harvester to determine the content of the material stream for the purposes described herein.

In FIG. 7 the drop heights and the velocities of the material streams onto each of the possible locations of the sensor 13 are different. The method and apparatus of the invention are capable of effectively distinguishing the different impact types, regardless of the drop height and velocity of the material stream (and hence regardless of the initial energy level of the impacting particles). This is primarily the result of the selection of dimensionless parameters of the algorithm of the method, and the arithmetic combinations contemplated within the scope of the invention.

For the avoidance of doubt, the possible locations of the sensor 13 are not limited to those shown in FIG. 7, these being exemplary only. Furthermore the method of the invention and the apparatus are useable in other installations than a combine harvester. Examples of suitable installations include but are not limited to conveyors, hoppers and silos.

In practical tests executed at the Laboratory for Agricultural Machinery and Processing of the Katholiek Universiteit Leuven, a grain loss sensor connected to a processor programmed to operate in accordance with the method of the invention achieved an overall discrimination accuracy 80% when distinguishing between grain impacts (on the one hand) and straw/straw tip impacts grouped as a single impact type (on the other hand); and an overall accuracy of 82% when distinguishing between grain impacts, straw impacts and straw tip impacts separately. As used herein, "overall accuracy" relates to the percentage of impacts correctly identified during a test period.

The invention claimed is:

1. A method of determining the content of a desired component in a stream of material including two or more types of component, comprising the steps of:

causing the stream, comprising plural particles of material, to impact a sensor member located in a path of the material thereby inducing vibration of the sensor member;

analysing vibrations of the sensor member and from the analysis determining whether individual impacts caused by the stream are one of any two or more types selected from three possible impact types, wherein the three impact types are grain impacts, straw impacts and straw tip impacts; and performing an operation based on the result of the analysis, wherein the step of performing an operation includes the steps of generating a grain loss signal indicative of the amount of grain in the stream and a MOG signal that is indicative of the amount of material other than grain (MOG) in the stream, and correcting the grain loss signal in dependence on the MOG signal.

2. A method according to claim 1 wherein the step of analysing vibrations of the sensor member includes analysing its vibrations in a frequency range exceeding 25 kHz.

3. A method according to claim 1 wherein the step of analysing vibrations of the sensor member includes analysing its vibrations in a frequency range of up to 50 kHz.

4. A method according to claim 1 wherein the MOG signal includes one or more components indicative of straw impacts and one or more components indicative of straw tip impacts.

5. A method according to claim 1 including the step of causing a display device to display information related to the grain loss signal.

6. A method according to claim 1 including the step of generating at least one control command in dependence on at least one of the grain loss signal and the MOG signal.

7. A method according to claim 6 wherein the at least one control command is selected from at least one of a cleaning section sieve opening command, a cleaning section sieve closing command and a fan speed command.

8. A method according to claim 1 wherein the sensor member includes a transducer that is capable of generating electrical signals that are indicative of its vibration; wherein the method includes deriving from the electrical signals variables that are related to vibrations of the sensor member; and wherein the step of analysing vibrations of the sensor member includes the step of processing the variables according to an algorithm containing arithmetic terms and parameters, the parameters being related to characteristics of three different types of impact respectively.

9. A method according to claim 8 including the step of making at least one of linear combinations of the processed variables and non-linear combinations of the processed variables.

10. A method according to claim 8 wherein the parameters of the algorithm are at least one of selected and combined as a result of at least one of Genetic algorithm techniques, Linear regression techniques, non-linear regression techniques, Tree-based modelling, Analysis of variance techniques and Canonical discrimination.

11. A method according to claim 8 wherein the variables relate to the vibration of the sensor member in two consecutive periods following impact of a particle of the stream of material.

12. A method according to claim 11 wherein the variables relate to the variance in the vibration of the plate during the two consecutive periods.

13. A method according to claim 12 wherein the two consecutive periods are the first and second half-milliseconds following impact.

14. A method according to claim 11 wherein in the algorithm the variable related to vibration in the first of the consecutive periods is subtracted from the variable related to vibration in the second period.

15. A method according to claim 11 wherein in the algorithm the variable related to vibration in the second period is divided by the variable related to vibration in the first period.

16. A method according to claim 9 wherein the variables are respectively related to the energy of vibration of the sensor member in upper and lower, distinct frequency bands.

17. A method according to claim 16 wherein in the algorithm the variable related to the energy of vibration in the upper frequency band is divided by the variable related to the energy of vibration in the lower frequency band or vice versa.

18. A method according to claim 16 wherein the upper frequency band is 30-40 kHz, and the lower frequency band is 2-10 kHz.

19. An apparatus for determining the content of MOG in a stream of material including a plurality of particles of materials, comprising:

a sensor member disposed within a path of the stream of material, wherein the sensor member is vibrative when impacted by the stream of material and having operatively connected thereto a transducer that is capable of generating one or more signals in dependence on vibration of the sensor member; and a processor that is operatively connected to receive the signals from the transducer and is programmed to analyse vibrations of the sensor member and from the analysis determining whether individual impacts caused by the stream are one of any two or more types selected from three possible impact types, wherein the three impact types are grain impacts, straw impacts and straw tip impacts and includes generating a grain loss signal indicative of the amount of grain in the stream and a MOG signal that is indicative of the amount of material other than grain (MOG) in the stream, and corrects the grain loss signal in dependence on the MOG signal.

* * * * *